(12) United States Patent
Yoon et al.

(10) Patent No.: US 10,770,662 B2
(45) Date of Patent: Sep. 8, 2020

(54) ORGANIC COMPOUND, ORGANIC LIGHT EMITTING DIODE AND ORGANIC LIGHT EMITTING DISPLAY DEVICE

(71) Applicants: LG Display Co., Ltd., Seoul (KR); Korea University Research and Business Foundation, Seoul (KR)

(72) Inventors: Dae-Wi Yoon, Paju-si (KR); Jun-Yun Kim, Goyang-si (KR); Dong-Hoon Choi, Seoul (KR); Su-Na Choi, Seoul (KR)

(73) Assignees: LG Display Co., Ltd., Seoul (KR); Korea University Research And Business Foundation, Seoul (KR)

( * ) Notice: Subject to any disclaimer, the term of this patent is extended or adjusted under 35 U.S.C. 154(b) by 241 days.

(21) Appl. No.: 15/823,928

(22) Filed: Nov. 28, 2017

(65) Prior Publication Data
US 2018/0151811 A1    May 31, 2018

(30) Foreign Application Priority Data

Nov. 30, 2016   (KR) .................. 10-2016-0162201

(51) Int. Cl.
*H01L 51/50*    (2006.01)
*H01L 51/00*    (2006.01)
(Continued)

(52) U.S. Cl.
CPC ........ *H01L 51/0072* (2013.01); *C07D 401/14* (2013.01); *C09K 11/06* (2013.01);
(Continued)

(58) Field of Classification Search
None
See application file for complete search history.

(56) References Cited

U.S. PATENT DOCUMENTS

2007/0013295 A1*  1/2007  Matsuura ............ H01L 51/0067
                                              313/504
2012/0132900 A1*  5/2012  Fujita ................. H01L 51/5052
                                              257/40
2012/0252147 A1*  10/2012 Takahashi ............... H01L 51/56
                                              438/33

FOREIGN PATENT DOCUMENTS

CN           103262283 A       8/2013

OTHER PUBLICATIONS

Zhang, et al., Synthesis and Optical Properties of Novel Carbazole Derivatives Containing Pyridine Ring, J. Heterocyclic Chem. 2013, 51, 669-673. (Year: 2013).*

(Continued)

*Primary Examiner* — Gregory D Clark
(74) *Attorney, Agent, or Firm* — Morgan, Lewis & Bockius LLP

(57) ABSTRACT

The present invention provides an organic compound of following formula and an organic light emitting diode and an OLED device including the organic compound.

(Continued)

100

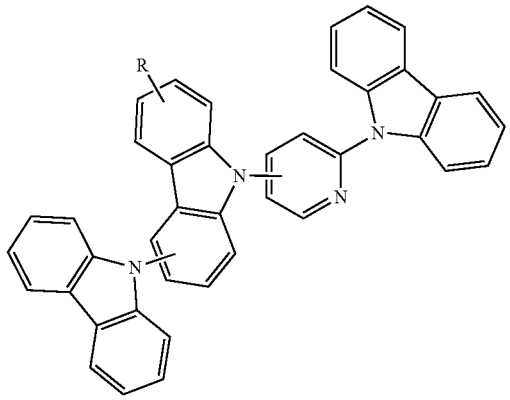

11 Claims, 6 Drawing Sheets

(51) Int. Cl.
*C07D 401/14* (2006.01)
*C09K 11/06* (2006.01)
*H01L 27/32* (2006.01)

(52) U.S. Cl.
CPC ...... *H01L 27/3258* (2013.01); *H01L 51/0067* (2013.01); *C09K 2211/1018* (2013.01); *H01L 27/3244* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 2251/552* (2013.01)

(56) References Cited

OTHER PUBLICATIONS

Su, Ruifei .et al.L.; Synthesis and Optical Properties of Novel Carbazole Derivatives Containing Pyridine Ring; Journal of Heterocyclic Chemistry (2014), 51(3), 669-673 (Year: 2014).*

Zhang et al., "Multiphosphine-Oxide Hosts for Ultralow-Voltage-Driven True-Blue Thermally Activated Delayed Fluorescence Diodes with External Quantum Efficiency beyond 20%", Advanced Materials, vol. 28, pp. 479-485 (2016).

Jianyong Zhao, Organic Light Emitting Diode (OLED) Display Technology, pp. 1-10, Jul. 31, 2012 (see the figures therein and the citation by the Search Report).

Search Report issued in Chinese Patent Application No. 201711227506.6 dated Feb. 25, 2020.

* cited by examiner

ORGANIC COMPOUND, ORGANIC LIGHT EMITTING DIODE AND ORGANIC LIGHT EMITTING DISPLAY DEVICE

The present application claims the benefit of Korean Patent Application No. 10-2016-0162201 filed in Korea on Nov. 30, 2016, which is herein incorporated by reference.

BACKGROUND

Technical Field

The present disclosure relates to an organic compound and an organic light emitting diode and more particularly to an organic compound having high triplet energy and long lifetime and an organic light emitting diode and an organic light emitting display (OLED) device using the same.

Discussion of the Related Art

Recently, requirement for flat panel display devices having small occupied area is increased. Among the flat panel display devices, an OLED device, which may be called to as an organic electroluminescent device, is widely introduced.

The OLED device emits light by injecting electrons from a cathode as an electron injection electrode and holes from an anode as a hole injection electrode into an organic emitting layer, combining the electrons with the holes, generating an exciton, and transforming the exciton from an excited state to a ground state. A flexible substrate, for example, a plastic substrate, can be used as a base substrate where elements are formed. Since the OLED device does not require a backlight assembly, the OLED device has low weight and low power consumption. Moreover, the OLED device can be operated at a voltage (e.g., 10V or below) lower than a voltage required to operate other display devices. In addition, the OLED device is adequate to produce full-color images.

The organic emitting layer may have a single-layered structure. Alternatively, to improve the emission efficiency, the organic emitting layer may have a multi-layered structure. For example, the organic emitting layer may include a hole injection layer (HIL), a hole transporting layer (HTL), an emitting material layer (EML), an electron transporting layer (ETL) and an electron injection layer (EIL).

The EML includes a dopant as an emitter. However, since the emission efficiency of the dopant is rapidly decreased by a concentration quenching problem, there is a limitation in the OLED device including the EML with only dopant. Accordingly, the EML further includes a host having a triplet energy greater than the dopant.

For example, in the organic light emitting diode including a phosphorescent emitting material, the hole from the anode and the electron from the cathode are combined in the host, and a single exciton formed in the host is transferred into a single state or a triplet state of the dopant. In addition, a triplet exciton in the host is transferred into the triplet state of the dopant.

For efficient energy transfer from the host into the dopant, the triplet energy of the host is required to be greater than that of the dopant. When the triplet energy of the host is smaller than that of the dopant, the energy reverse-transfer from the dopant into the host is generated such that the emission efficiency is decreased.

For example, for the blue emission, the host having high triplet energy (T1>3.0 eV) is required, and phosphineoxide-based compound of Formula 1-1 or Formula 1-2 may be used for the blue host.

[Formula 1-1]

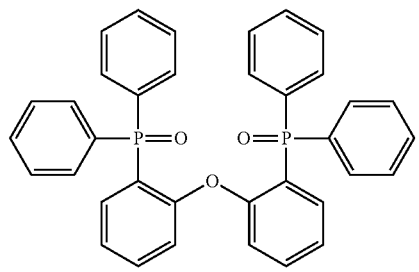

[Formula 1-2]

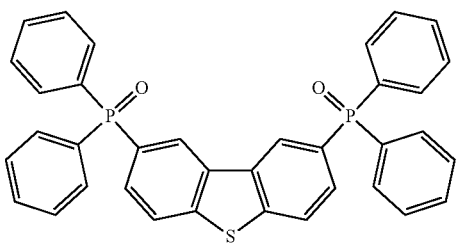

However, the host of Formula 1-1 and/or Formula 1-2 has low stability such that the organic light emitting diode has very short lifetime.

Namely, since an bonding energy between a carbon atom (C) in the benzene ring and a phosphorous atom (P) is lower than the energy of the blue light, the host compound is decomposed during the operation of the organic light emitting diode.

Accordingly, there is a limitation in the above host for the display device.

SUMMARY

Accordingly, embodiments of the present disclosure are directed to an organic compound, an organic light emitting diode, and an OLED device using the same that substantially obviate one or more of the problems due to limitations and disadvantages of the related art.

An aspect of the present disclosure is to provide an organic compound having high triplet energy and stability.

Another aspect of the present disclosure is to provide an organic light emitting diode and an OLED having improved emission efficiency and lifetime Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

To achieve these and other aspects of the inventive concepts, as embodied and broadly described herein, the present disclosure provides an organic compound of following formula:

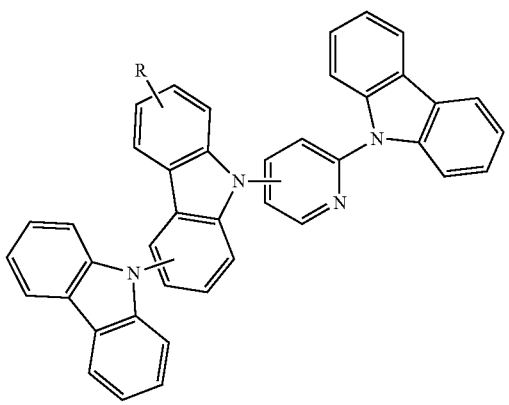

wherein R is selected from the group consisting of hydrogen and carbazole.

In another aspect, an organic light emitting diode comprises a first electrode; a second electrode facing the first electrode; an emitting material layer between the first and second electrodes and including an organic compound, the organic compound having following formula:

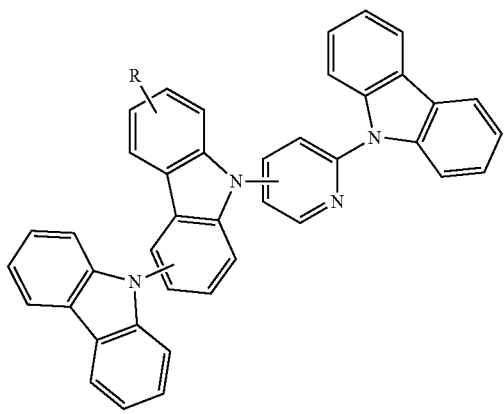

wherein R is selected from the group consisting of hydrogen and carbazole.

In another aspect, an organic light emitting display device comprises a substrate; an organic light emitting diode over the substrate and including a first electrode, a second electrode facing the first electrode and an organic emitting layer between the first and second electrodes; and a thin film transistor between the substrate and the organic light emitting diode and connected to the organic light emitting diode, wherein the organic emitting layer includes an organic compound of following formula:

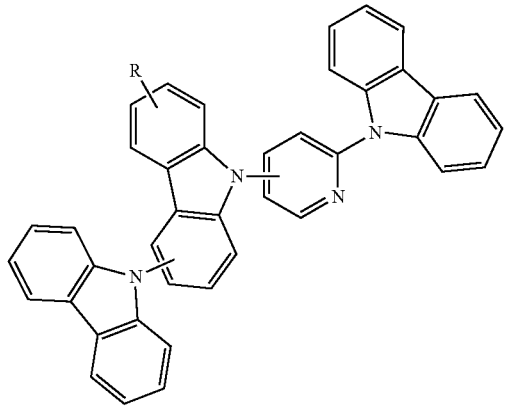

and wherein R is selected from the group consisting of hydrogen and carbazole.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure and are incorporated and constitute a part of this application, illustrate embodiments of the disclosure and together with the description serve to explain various principles.

DETAILED DESCRIPTION

Reference will now be made in detail to embodiments of the present application, examples of which are illustrated in the accompanying drawings.

Figure 1:
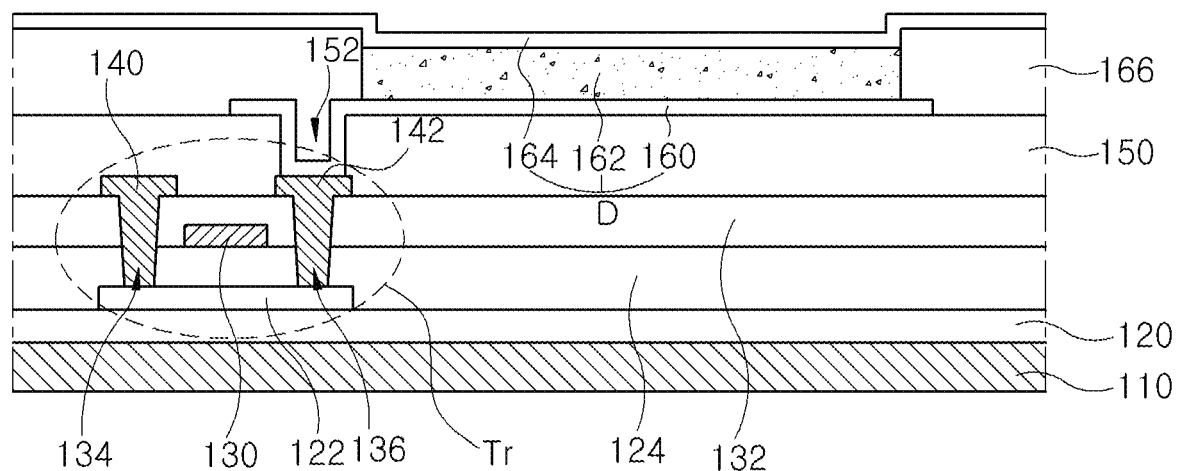
FIG. 1 is a schematic cross-sectional view of an OLED device according to the present invention.
Figure 2:
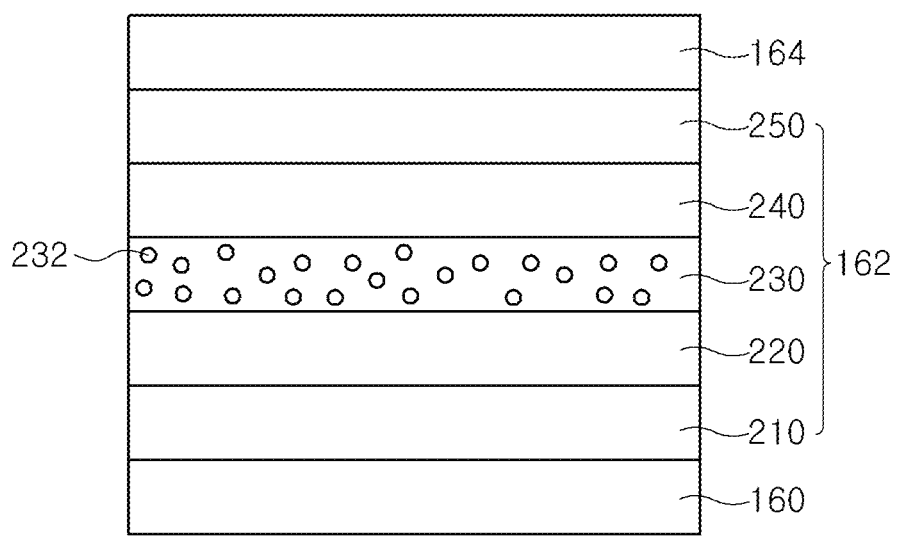
FIG. 2 is a schematic cross-sectional view of an organic light emitting diode according to the present invention.

FIG. 1 is a schematic cross-sectional view of an OLED device according to the present invention, and FIG. 2 is a schematic cross-sectional view of an organic light emitting diode according to the present invention.

As shown in FIGS. 1 and 2, an OLED device 100 includes a substrate 110, an organic light emitting diode D over the substrate 110, a thin film transistor (TFT) Tr between the substrate 110 and the organic light emitting diode D. The TFT Tr is connected to the organic light emitting diode D.

The substrate 110 may be a glass substrate or a flexible plastic substrate.

A buffer layer 120 is formed on the substrate 110, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 may be shielded or blocked by the light-shielding pattern such that thermal degradation of the semiconductor layer 122 can be prevented. When the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 above a center of the semiconductor layer 122.

In FIG. 1, the gate insulating layer 124 is formed on the entire surface of the substrate 110. Alternatively, the gate insulating layer 124 may be patterned to have the same shape or a similar shape as the gate electrode 130.

An interlayer insulating layer 132, which is formed of an insulating material, is formed on an entire surface of the substrate 110 including the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

In FIG. 1, the first and second contact holes 134 and 136 extend into the gate insulating layer 124. Alternatively, when the gate insulating layer 124 is patterned to have the same shape as the gate electrode 130, the first and second contact holes 134 and 136 are formed only through the interlayer insulating layer 132 and not through the gate insulating layer 124.

A source electrode 140 and a drain electrode 142, which are formed of a conductive material, e.g., metal, are formed on the interlayer insulating layer 132. The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr, and the TFT Tr serves as a driving element.

In FIG. 1, the gate electrode 130, the source electrode 140 and the drain electrode 142 are positioned over the semiconductor layer 122. Namely, the TFT Tr has a coplanar structure. Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, a gate line and a data line are disposed on or over the substrate 110 and cross each other to define a pixel region. In addition, a switching element, which is electrically connected to the gate line and the data line, may be disposed on the substrate 110. The switching element is electrically connected to the TFT Tr as the driving element.

In addition, a power line, which is parallel to and spaced apart from the gate line or the data line, may be formed on or over the substrate 110. Moreover, a storage capacitor for maintaining a voltage of the gate electrode 130 of the TFT Tr during one frame, may be further formed on the substrate 110.

A passivation layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel region. The first electrode 160 may be an anode and may be formed of a conductive material having a relatively high work function. For example, the first electrode 160 may be formed of a transparent conductive material such as indium-tin-oxide (ITO) or indium-zinc-oxide (IZO).

When the organic emitting diode D is operated in a top-emission type, a reflection electrode or a reflection layer may be formed under the first electrode 160. For example, the reflection electrode or the reflection layer may be formed of aluminum-palladium-copper (APC) alloy.

A bank layer 166, which covers edges of the first electrode 160, is formed on the passivation layer 150. A center of the first electrode 160 in the pixel region is exposed through an opening of the bank layer 166.

An organic emitting layer 162 is formed on the first electrode 160. The organic emitting layer 162 may have a single-layered structure of an emitting material layer (EML) formed of an emitting material. Alternatively, to improve emitting efficiency, the organic emitting layer 162 may have a multi-layered structure further including at least one auxiliary layer.

Referring to FIG. 2, the organic emitting layer (162) may include EML 230 between the first and second electrodes 160 and 164, an HTL 220 between the first electrode 160 and the EML 230, an HIL 210 between the first electrode 160 and the HTL 220, an ETL 240 between the EML 230 and the second electrode 164 and an EIL 250 between the ETL 240 and the second electrode 164.

In addition, the organic emitting layer 162 may further include an electron blocking layer (EBL, not shown) between the HTL 220 and the EML 230 and a hole blocking layer (HBL, not shown) between the EML 230 and the ETL 240.

A second electrode 164 is formed over the substrate 110 including the organic emitting layer 162. The second electrode 164 is positioned at an entire surface of the display area. The second electrode 164 may be a cathode. The second electrode 164 may be formed of a conductive material having a a lower work function than the first electrode 160. For example, the second electrode 164 may be formed of aluminum (Al), magnesium (Mg) or Al—Mg alloy.

The first electrode 160, the organic emitting layer 162 and the second electrode 164 constitute the organic light emitting diode D.

Although not shown, an encapsulation film is formed on the organic light emitting diode D to prevent penetration of moisture into the organic light emitting diode D. The encapsulation film may have has a triple-layered structure of a first inorganic layer, an organic layer and a second inorganic layer. However, it is not limited thereto. For example, the encapsulation film 180 may further include an organic layer on the second inorganic layer 186 or an organic layer and an inorganic layer stacked on the second inorganic layer 186.

In addition, a polarization plate for reducing an ambient light reflection may be disposed over the top-emission type organic light emitting diode D. For example, the polarization plate may be a circular polarization plate.

In the organic light emitting diode D and/or the OLED device 100, the organic emitting layer 162, preferably the EML 230 includes an organic compound 232 of Formula 2.

[Formula 2]

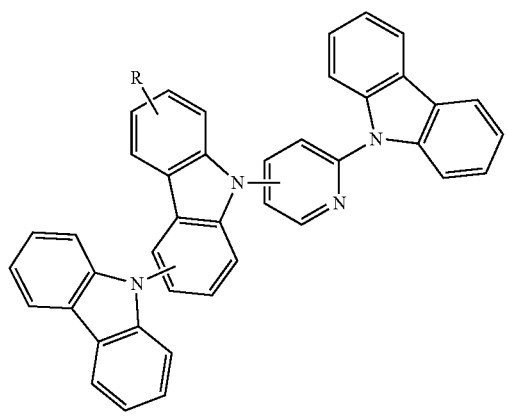

In Formula 2, R is selected from the group consisting of hydrogen and carbazole.

Namely, the organic compound 232 includes at least three carbazole moieties directly or indirectly connected (combined or linked) to a pyridine core. A single carbazole moiety is connected to an ortho-position of the pyridine core, and a dual carbazole moiety, i.e., a carbazole moiety substituted by carbazole (carbazole-substituted carbazole moiety), is connected to a position of the pyridine core to be spaced apart from the single carbazole moiety with at least one carbon atom or a nitrogen atom of the pyridine core between the single carbazole moiety and the dual carbazole moiety.

In other words, the carbon atoms in the pyridine core are sequentially defined as C1, C2, C3, C4 and C5 relative to the nitrogen atom of the pyridine core, the single carbazole moiety is connected to C1 carbon atom, the dual carbazole moiety is connected to one of C3 to C5 carbon atoms. In Formula 2, the R-substituted carbazole moiety has a meta-position or a para-position with respect to the single carbazole moiety.

The organic compound 232 of the present invention may be selected from Formula 3.

[Formula 3]

H-1

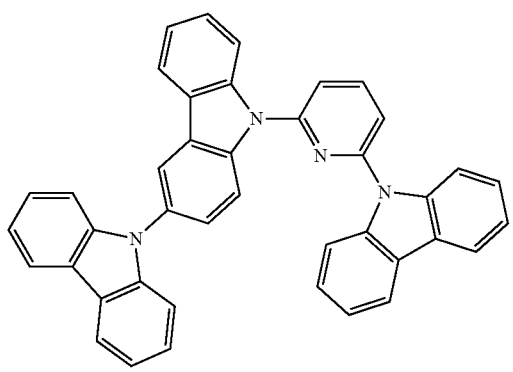

H-2

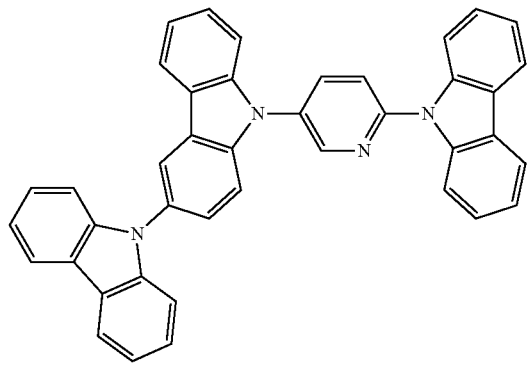

H-3

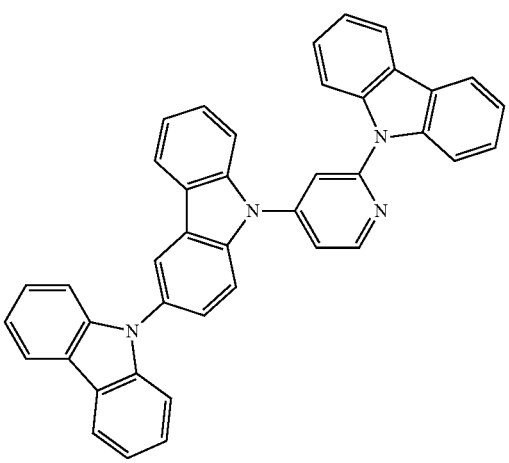

H-4

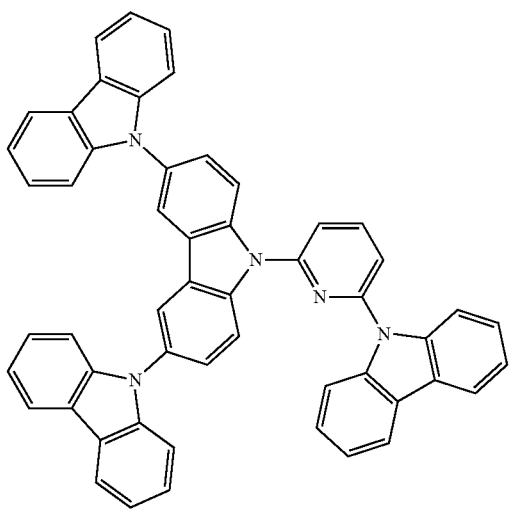

H-5

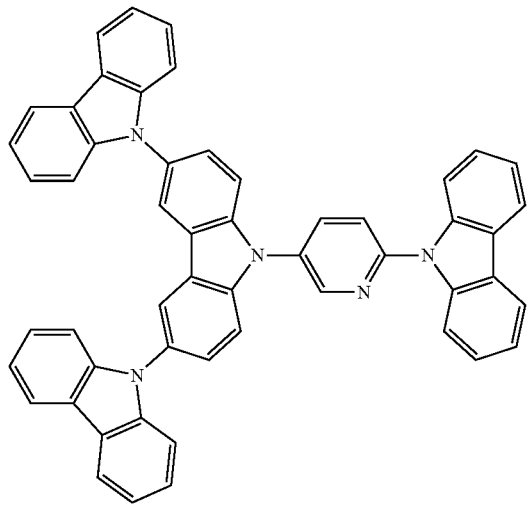

[Formula 4]

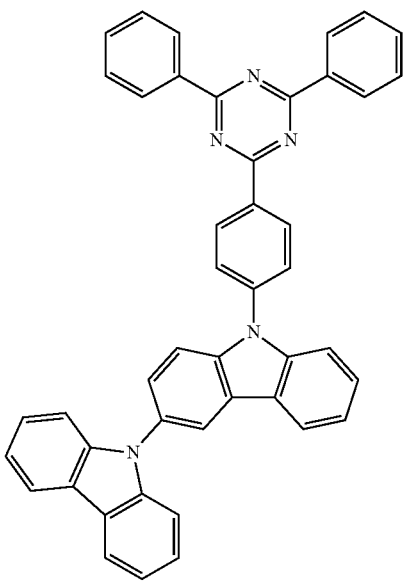
D-1

H-6

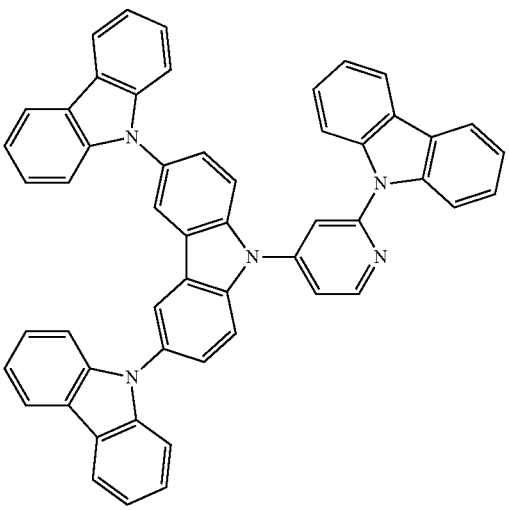

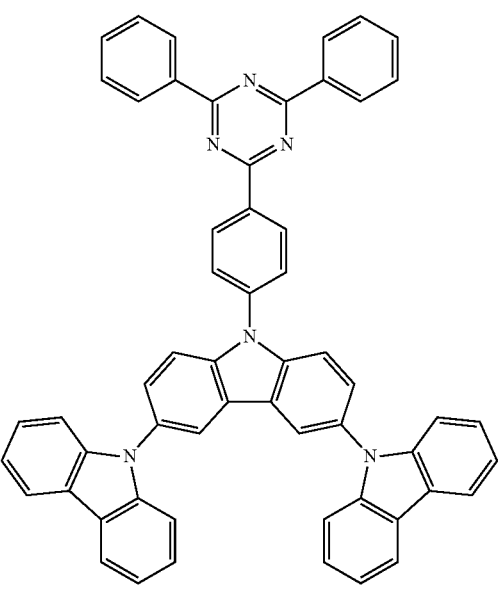
D-2

The organic compound 232 has high triplet energy and improved stability.

The organic compound 232 is used as a host of the EML 230, and the EML 230 further includes a dopant.

The dopant may have a triplet energy being smaller than the organic compound 232 and has a weight % of about 1 to 30 with respect to the host. The dopant may be a fluorescent material, a phosphorescent material or a thermally activated delayed fluorescent (TADF) material.

For example, the TADF material as the dopant may be selected from Formula 4.

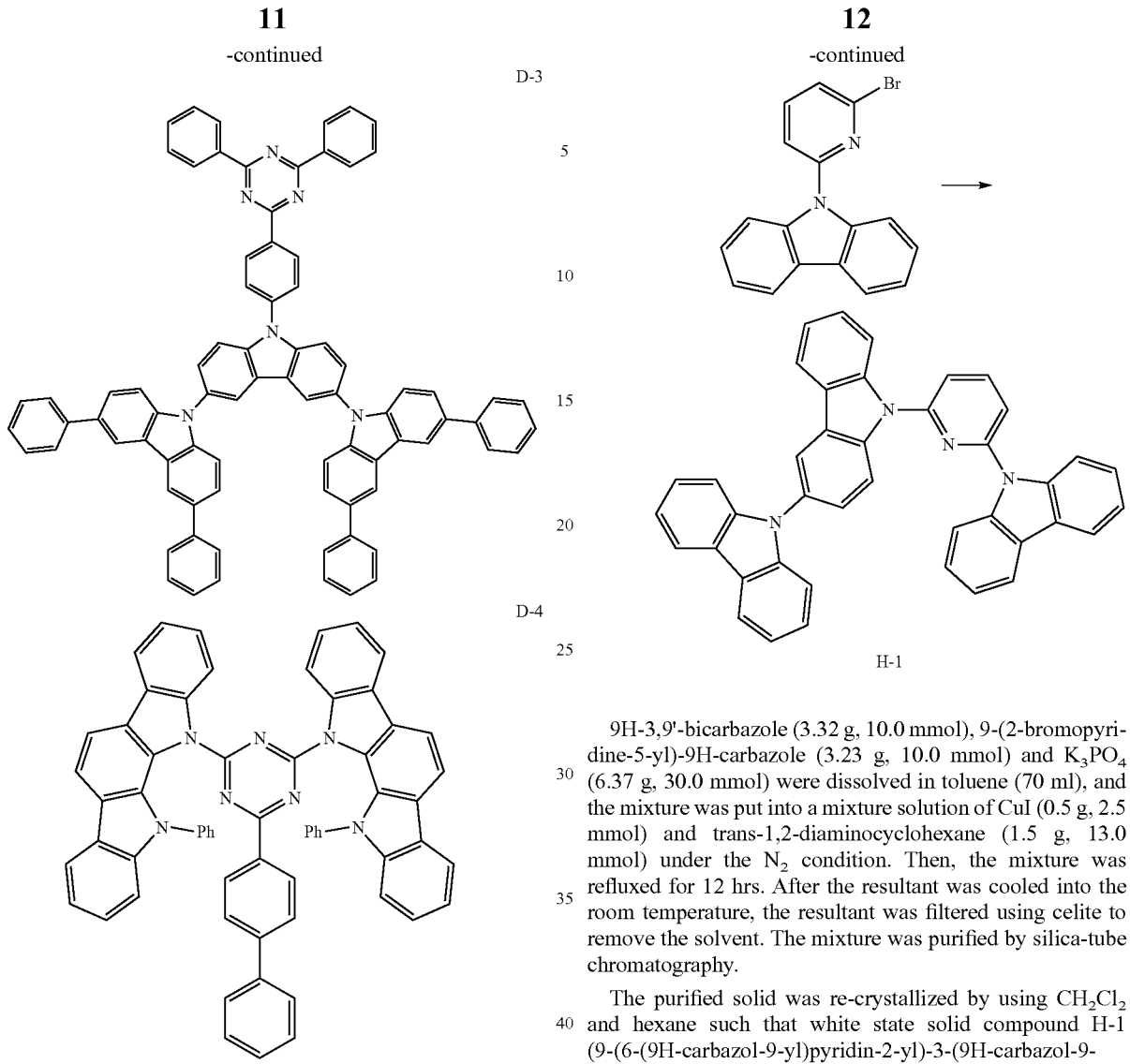

As mentioned above, since the organic compound has high triplet energy and improved stability, the organic light emitting diode D and/or the OLED device 100 has high emission efficiency and improved lifetime.

Synthesis of the Organic Compound

1. Compound H-1

[Reaction Formula 1]

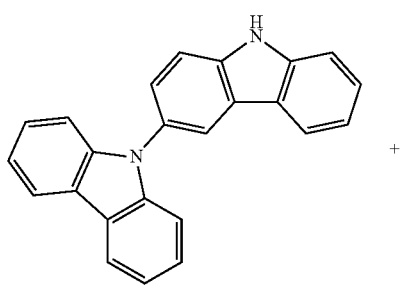

9H-3,9'-bicarbazole (3.32 g, 10.0 mmol), 9-(2-bromopyridine-5-yl)-9H-carbazole (3.23 g, 10.0 mmol) and $K_3PO_4$ (6.37 g, 30.0 mmol) were dissolved in toluene (70 ml), and the mixture was put into a mixture solution of CuI (0.5 g, 2.5 mmol) and trans-1,2-diaminocyclohexane (1.5 g, 13.0 mmol) under the $N_2$ condition. Then, the mixture was refluxed for 12 hrs. After the resultant was cooled into the room temperature, the resultant was filtered using celite to remove the solvent. The mixture was purified by silica-tube chromatography.

The purified solid was re-crystallized by using $CH_2Cl_2$ and hexane such that white state solid compound H-1 (9-(6-(9H-carbazol-9-yl)pyridin-2-yl)-3-(9H-carbazol-9-yl)-9H-carbazole) was obtained. (4.98 g, 8.68 mmol, 87%)

Figure 3A:
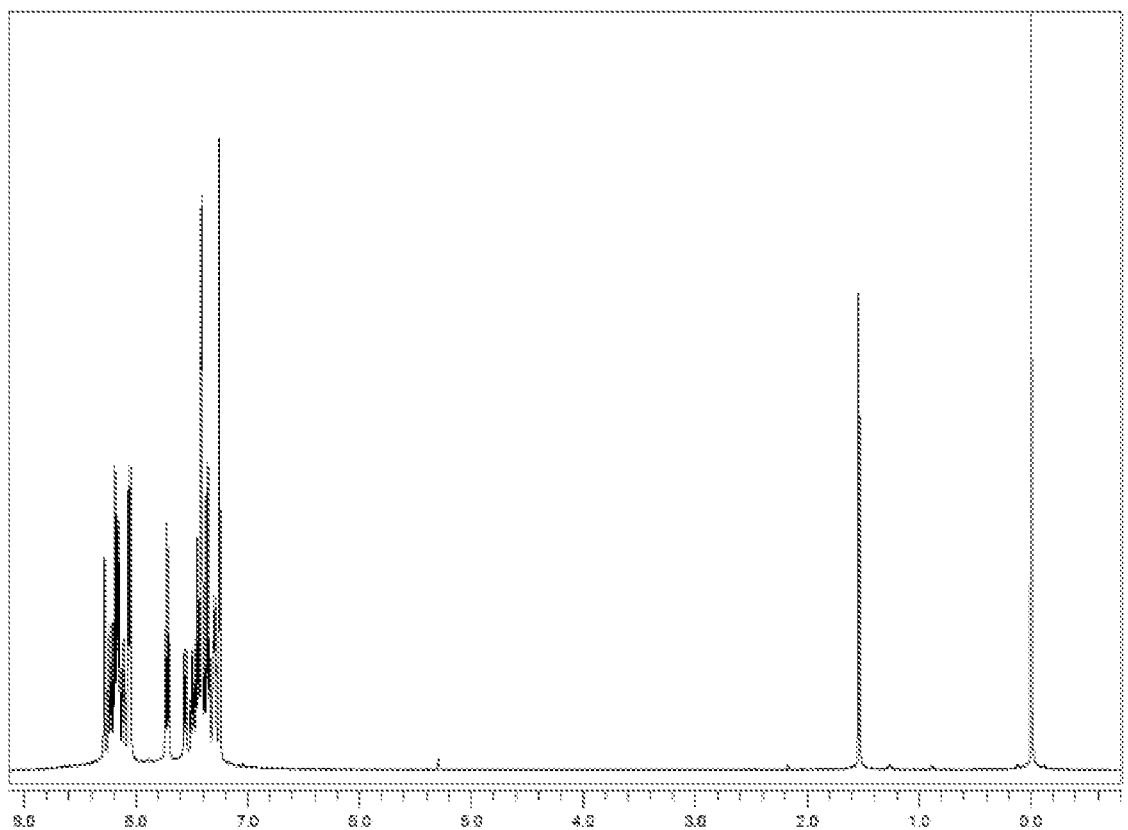
FIGS. 3A to 3E are NMR graphs of organic compounds according to the present invention.

FIG. 3A shows the NMR graph of the compound H-1. ($^1$H-NMR (500 MHz, CDCl3): δ(ppm) 8.28 (s, 1H), 8.25-8.14 (m, 6H), 8.12-8.10 (d, J=7.65 Hz, 1H), 8.07-8.05 (d, J=8.55 Hz, 2H), 7.74-7.70 (t, J=8.20 Hz, 2H), 7.57-7.55 (d, J=8.55 Hz, 1H), 7.51-7.28 (m, 13H). Anal. Calcd. for $C_{41}H_{26}N_4$: C, 85.69; H, 4.56; N, 9.75, found: C, 85.57; H, 4.61; N, 9.82).

2. Compound H-2

[Reaction Formula 2]

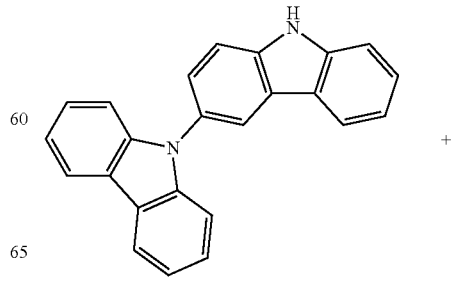

-continued

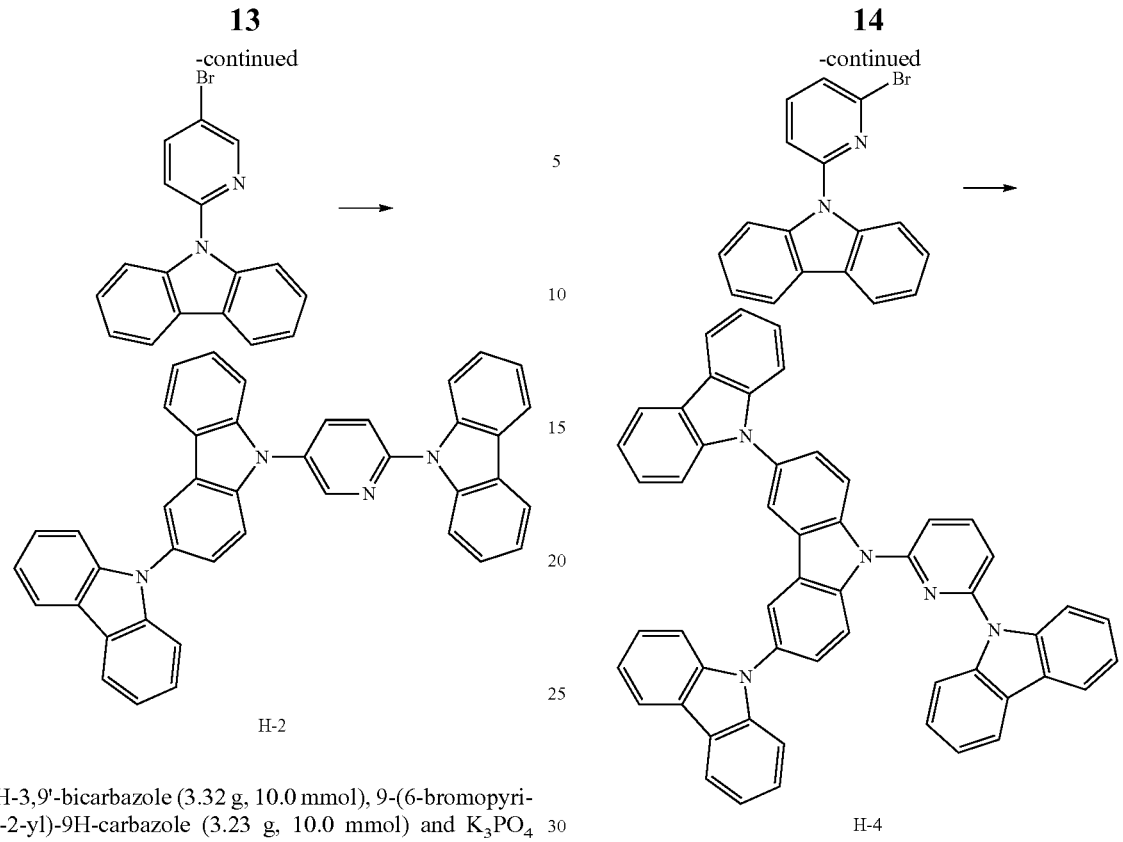

H-2

9H-3,9'-bicarbazole (3.32 g, 10.0 mmol), 9-(6-bromopyridine-2-yl)-9H-carbazole (3.23 g, 10.0 mmol) and K$_3$PO$_4$ (6.37 g, 30.0 mmol) were dissolved in toluene (70 ml), and the mixture was put into a mixture solution of CuI (0.5 g, 2.5 mmol) and trans-1,2-diaminocyclohexane (1.5 g, 13.0 mmol) under the N$_2$ condition. Then, the mixture was refluxed for 12 hrs. After the resultant was cooled into the room temperature, the resultant was filtered using celite to remove the solvent. The mixture was purified by silica-tube chromatography.

The purified solid was re-crystallized by using CH$_2$Cl$_2$ and hexane such that white state solid compound H-2 (9-(6-(9H-carbazol-9-yl)pyridin-2-yl)-9H-3,9'-bicarbazole) was obtained. (4.89 g, 8.51 mmol, 85%)

Figure 3B:
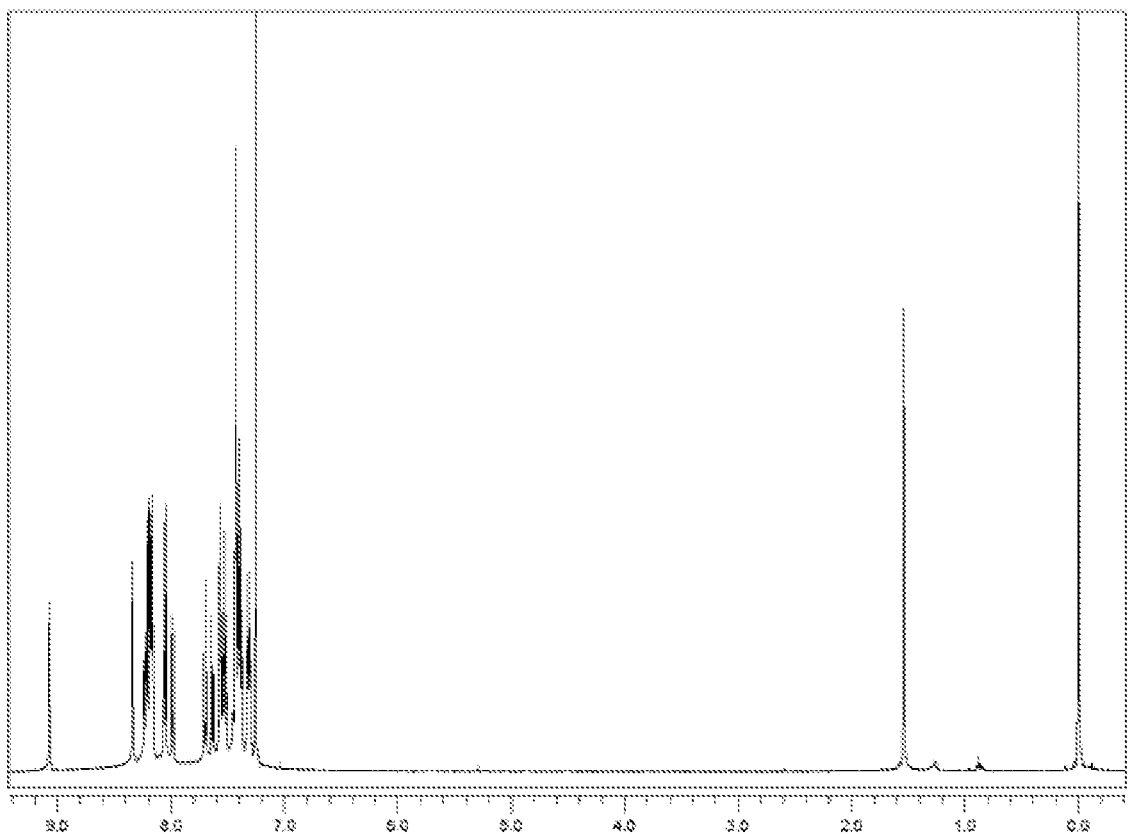

FIG. 3B shows the NMR graph of the compound H-2. ($^1$H-NMR (500 MHz, CDCl$_3$): δ(ppm) 9.07 (d, J=2.15 Hz, 1H), 8.34 (d, J=1.50 Hz, 1H), 8.24-8.16 (m, 6H), 8.06-8.05 (d, J=1.51 Hz, 2H), 8.00-7.98 (d, J=8.50 Hz, 1H), 7.71-7.69 (d, J=8.55 Hz, 1H), 7.65-7.63 (dd, J=2.15, 8.55 Hz, 1H), 7.58-7.51 (m, 4H), 7.45-7.38 (m, 7H), 7.34-7.29 (m, 2H). Anal. Calcd. for C$_{41}$H$_{26}$N$_4$: C, 85.69; H, 4.56; N, 9.75, found: C, 85.59; H, 4.60; N, 9.81).

3. Compound H-4

[Reaction Formula 3]

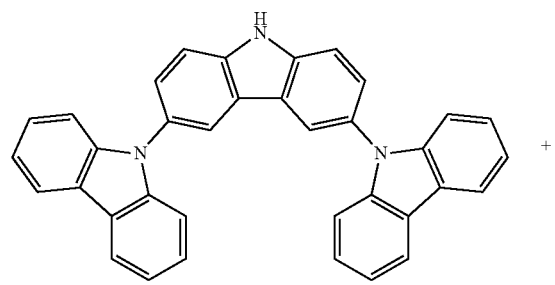

H-4

9'H-9,3': 6',9''-tercarbazole (4.98 g, 10.0 mmol), 9-(6-bromopyridine-2-yl)-9H-carbazole (3.23 g, 10.0 mmol) and K$_3$PO$_4$ (6.37 g, 30.0 mmol) were dissolved in toluene (70 ml), and the mixture was put into a mixture solution of CuI (0.5 g, 2.5 mmol) and trans-1,2-diaminocyclohexane (1.5 g, 13.0 mmol) under the N$_2$ condition. Then, the mixture was refluxed for 12 hrs. After the resultant was cooled into the room temperature, the resultant was filtered using celite to remove the solvent. The mixture was purified by silica-tube chromatography.

The purified solid was re-crystallized by using CH$_2$Cl$_2$ and hexane such that white state solid compound H-4 (9-(6-(9H-carbazol-9-yl)pyridin-2-yl)-3,6-di(9H-carbazol-9-yl)-9H-carbazole) was obtained. (5.65 g, 7.64 mmol, 76%)

Figure 3C:
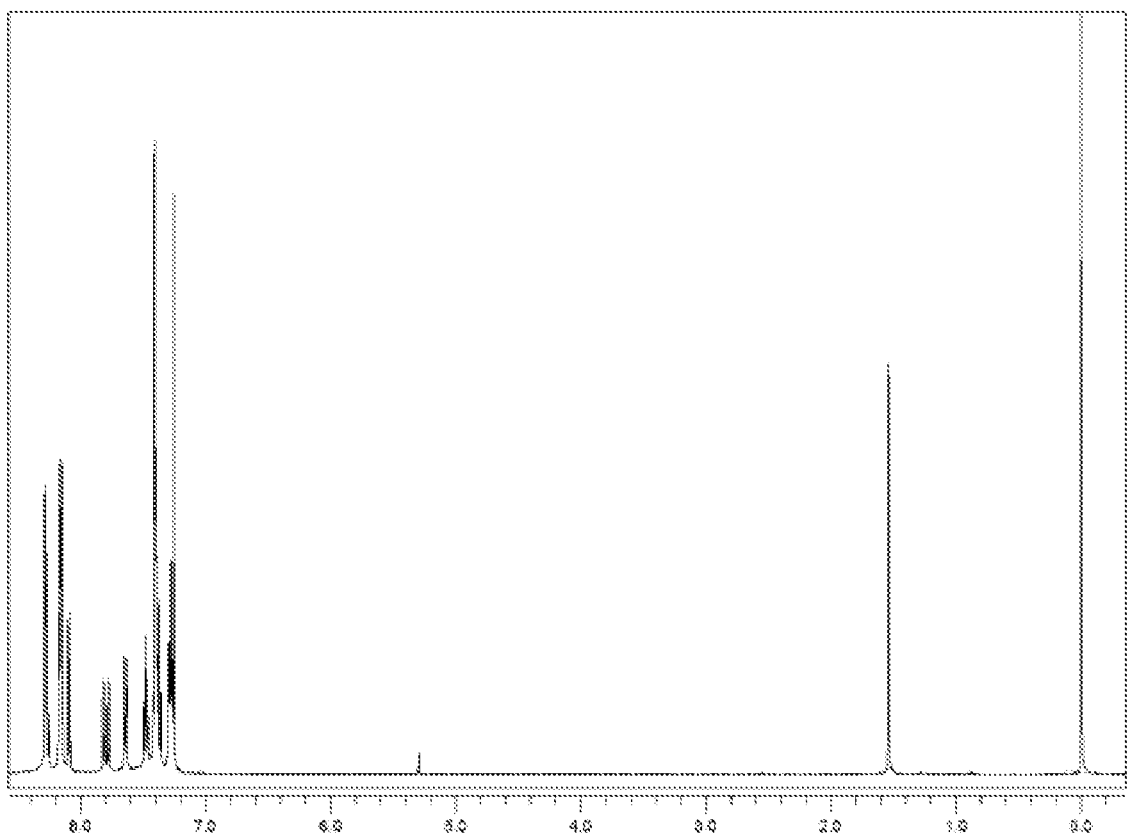

FIG. 3C shows the NMR graph of the compound H-4. ($^1$H-NMR (500 MHz, CDCl$_3$): δ(ppm) 8.29-8.25 (m, 5H), 8.17-8.15 (m, 6H), 8.10-8.08 (d, J=8.25 Hz, 2H), 7.82-7.81 (d, J=7.90 Hz, 1H), 7.79-7.77 (d, J=7.90 Hz, 1H), 7.65-7.63 (dd, J=1.80, 8.85 Hz, 2H), 7.49-7.46 (t, J=7.95 Hz, 2H), 7.42-7.36 (m, 10H), 7.31-7.26 (m, 4H). Anal. Calcd. for C$_{53}$H$_{33}$N$_5$: C, 86.04; H, 4.50; N, 9.47, found: C, 86.11; H, 4.35; N, 9.54).

4. Compound H-5

[Reaction Formula 4]

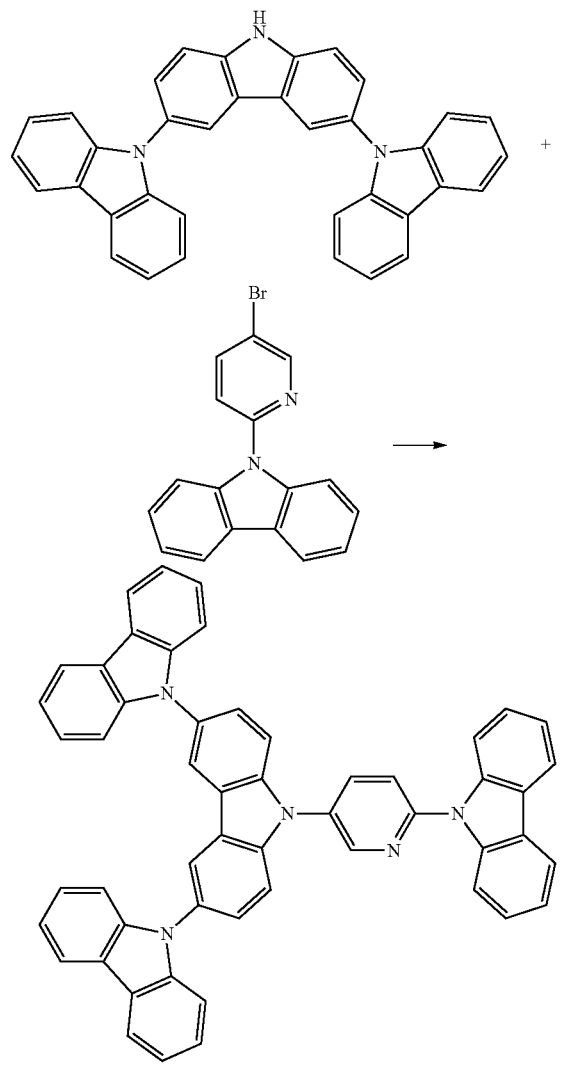

H-5

9'H-9,3':6',9''-tercarbazole (4.98 g, 10.0 mmol), 9-(5-Bromopyridine-2-yl)-9H-carbazole (3.23 g, 10.0 mmol), K$_3$PO$_4$ (6.37 g, 30.0 mmol) were dissolved in toluene (70 ml), and the mixture was put into a mixture solution of CuI (0.5 g, 2.5 mmol) and trans-1,2-diaminocyclohexane (1.5 g, 13.0 mmol) under the N$_2$ condition. Then, the mixture was refluxed for 12 hrs. After the resultant was cooled into the room temperature, the resultant was filtered using celite to remove the solvent. The mixture was purified by silica-tube chromatography.

The purified solid was re-crystallized by using CH$_2$Cl$_2$ and hexane such that white state solid compound H-5 (9-(6-(9H-carbazol-9-yl)pyridin-2-yl)-3,6-di(9H-carbazol-9-yl)-9H-carbazole) was obtained. (5.96 g, 8.05 mmol, 81%)

Figure 3D:
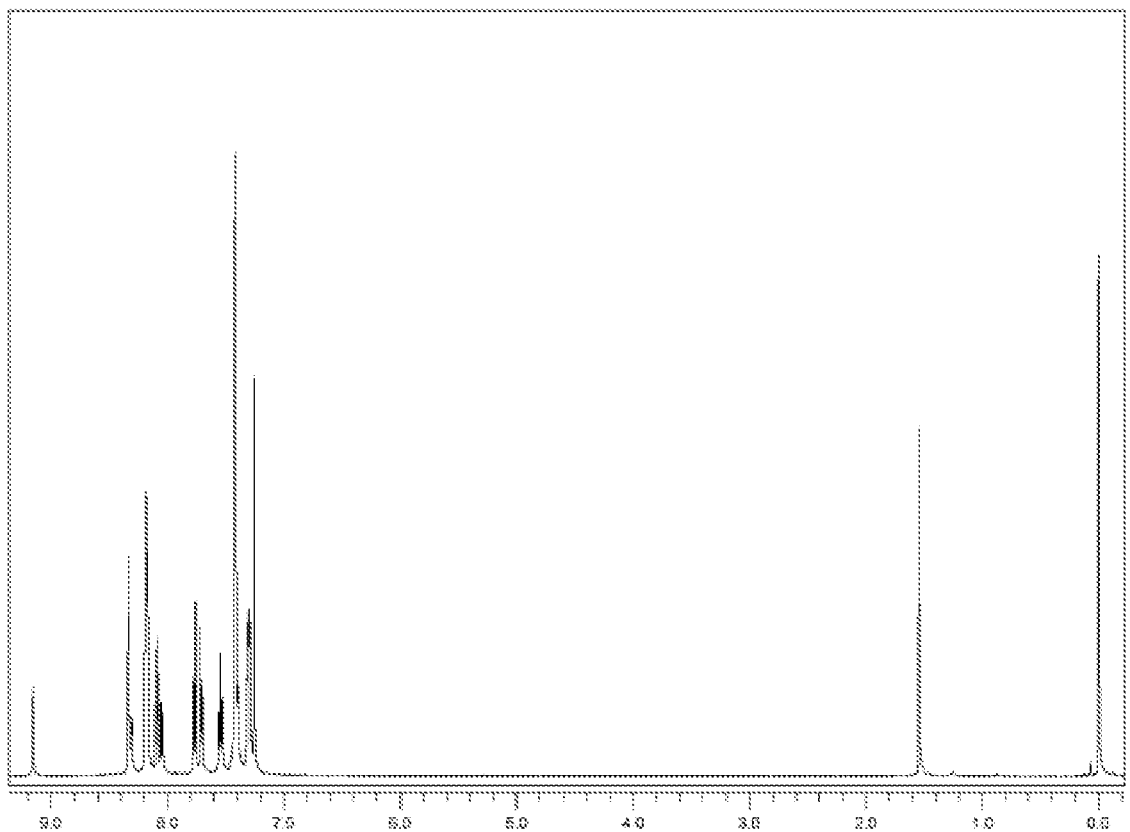

FIG. 3D shows the NMR graph of the compound H-5. ($^1$H-NMR (500 MHz, CDCl$_3$): δ(ppm) 9.16 (s, 1H), 8.34-8.31 (m, 3H), 8.19-8.17 (m, 6H), 8.10-8.08 (d, J=8.55 Hz, 2H), 8.06-8.04 (d, J=8.55 Hz, 1H), 7.78-7.76 (d, J=8.85 Hz, 2H), 7.72-7.70 (d, J=8.55 Hz, 2H), 7.56-7.53 (t, J=7.30 Hz, 2H), 7.43-7.39 (m, 10H), 7.32-7.29 (m, 4H). Anal. Calcd. for C$_{53}$H$_{33}$N$_5$: C, 86.04; H, 4.50; N, 9.47, found: C, 86.09; H, 4.44; N, 9.47).

5. Compound H-6

[Reaction Formula 5]

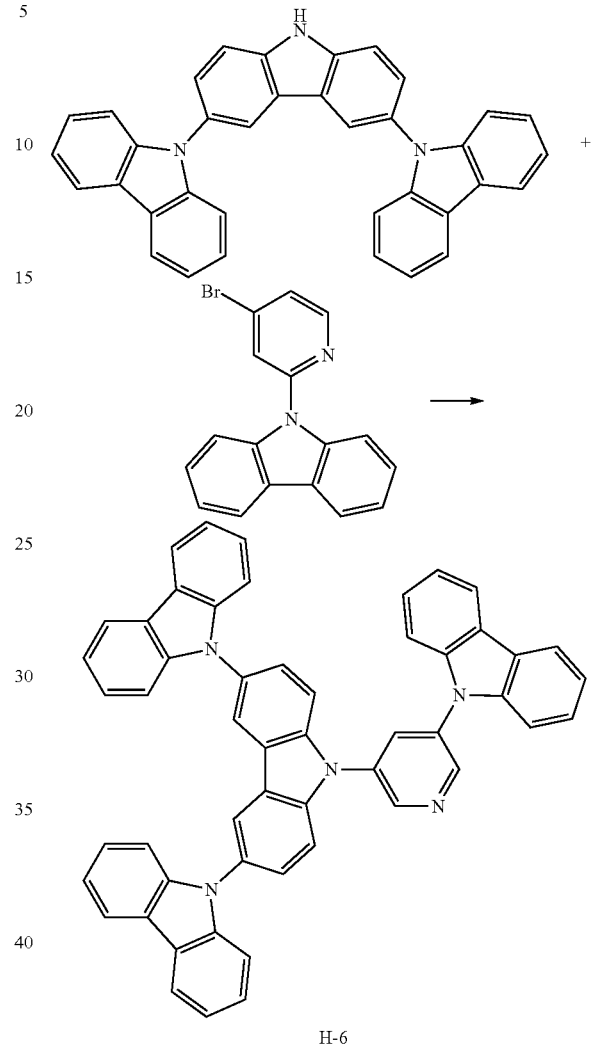

H-6

9'H-9,3':6',9''-tercarbazole (4.98 g, 10.0 mmol), 9-(6-Bromopyridine-2-yl)-9H-carbazole (3.23 g, 10.0 mmol), K$_3$PO$_4$ (6.37 g, 30.0 mmol) were dissolved in toluene (70 ml), and the mixture was put into a mixture solution of CuI (0.5 g, 2.5 mmol) and trans-1,2-diaminocyclohexane (1.5 g, 13.0 mmol) under the N$_2$ condition. Then, the mixture was refluxed for 12 hrs. After the resultant was cooled into the room temperature, the resultant was filtered using celite to remove the solvent. The mixture was purified by silica-tube chromatography.

The purified solid was re-crystallized by using CH$_2$Cl$_2$ and hexane such that white state solid compound H-6 (9-(6-(9H-carbazol-9-yl)pyridin-2-yl)-3,6-di(9H-carbazol-9-yl)-9H-carbazole) was obtained. (5.28 g, 7.14 mmol, 71%)

Figure 3E:
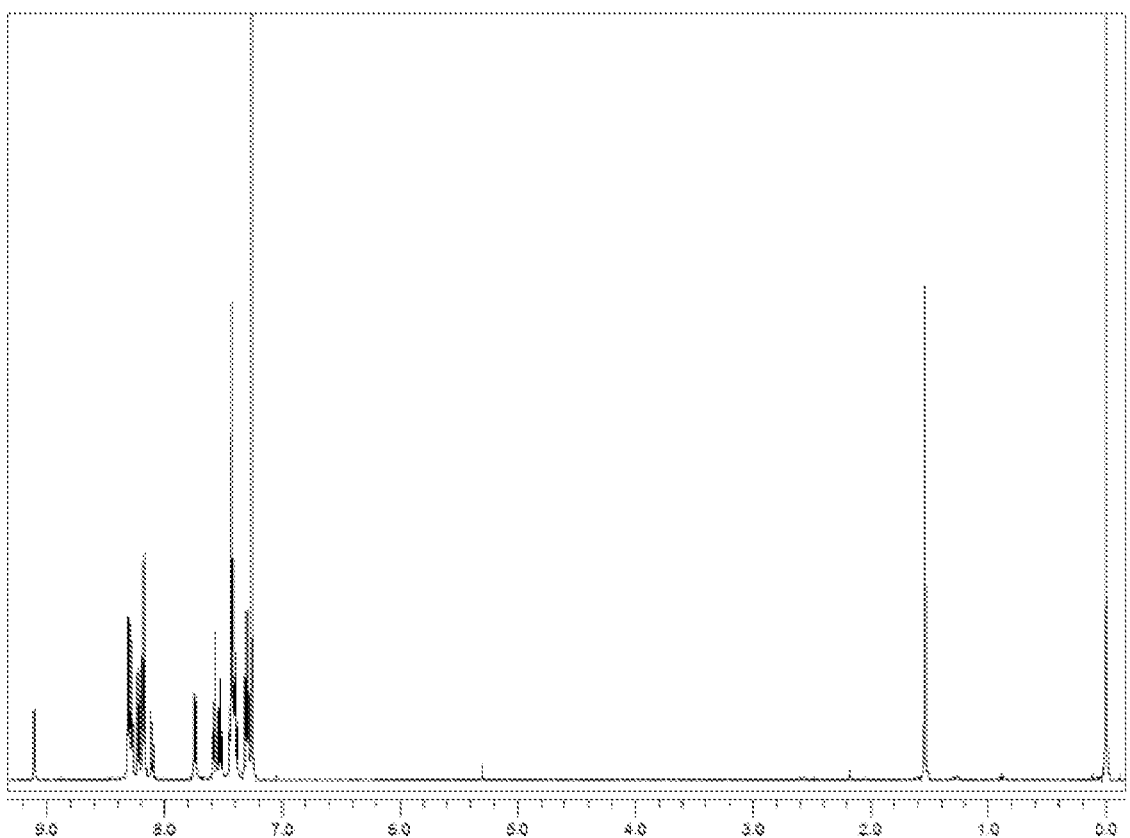

FIG. 3E shows the NMR graph of the compound H-6. ($^1$H-NMR (500 MHz, CDCl$_3$): δ(ppm) 9.11 (d, 1H, J=2.50 Hz), 8.31-8.27 (m, 5H), 8.22 (d, 2H, J=7.60 Hz), 8.19 (d, J=7.65 Hz, 2H), 8.10 (d, J=8.55 Hz, 1H), 7.75 (d, J=8.85 Hz, 2H), 7.59 (d, J=8.55 Hz, 2H), 7.54 (t, J=7.30 Hz, 2H), 7.45-7.38 (m, 10H), 7.32 (t, J=7.90 Hz, 4H). Anal. Calcd. for C$_{53}$H$_{33}$N$_5$: C, 86.04; H, 4.50; N, 9.47, found: C, 85.95; H, 4.52; N, 9.61).

The properties of the organic compounds are measured and listed in Table 1. (f: oscillator strength)

TABLE 1

| Compound | HOMO$^a$ | LUMO$^a$ | S1$^a$ | T1$^a$ | f$^a$ | HOMO$^b$ | LUMO$^c$ | Eg$^d$ |
|---|---|---|---|---|---|---|---|---|
| H-1 | −5.22 | −1.21 | 3.57 | 3.13 | 0.15 | −5.58 | −2.20 | 3.38 |
| H-2 | −5.20 | −1.31 | 3.45 | 3.11 | 0.14 | −5.58 | −2.24 | 3.34 |
| H-4 | −5.20 | −1.35 | 3.39 | 3.10 | 0.08 | −5.59 | −2.20 | 3.39 |
| H-5 | −5.24 | −1.42 | 3.37 | 3.04 | 0.00 | −5.62 | −2.28 | 3.34 |
| H-6 | −5.21 | −1.45 | 3.32 | 3.04 | 0.19 | −5.63 | −2.30 | 3.33 |

$^a$Simulation data using Gaussian 09 (DFT calculation, B3LYP/6-31G*)
$^b$Measured by cyclic voltammetry
$^c$LUMO = HOMO + Eg
$^d$Estimated from the absorption onset As shown in Table 1, the organic compound of the present invention has high triplet energy (T1) and wide band gap energy (Eg) such that the organic compound is adequate to the host of the EML.

[Organic Light Emitting Diode]

In the vacuum chamber, layers are deposited on an ITO substrate in an order below.
(a) the HIL 70 Å (Formula 5-1 compound),
(b) the HTL 550 Å (Formula 5-2 compound),
(c) the EBL 100 Å (Formula 5-3 compound),
(d) the EML 250 Å (host-dopant (D2 compound in Formula 4),
(e) the HBL 100 Å (Formula 5-4 compound),
(f) the ETL 100 Å (Formula 5-5 compound),
(g) the EIL 8 Å (LiF), and
(h) the cathode 800 Å (Al)

(1) Comparative Example 1

Formula 6-1 compound is used as the host in the EML.

(2) Comparative Example 2

Formula 6-2 compound is used as the host in the EML.

(3) Comparative Example 3

Formula 6-3 compound is used as the host in the EML.

(4) Comparative Example 4

Formula 6-4 compound is used as the host in the EML.

(5) Comparative Example 5

Formula 6-5 compound is used as the host in the EML.

(6) Comparative Example 6

Formula 6-6 compound is used as the host in the EML.

(7) Comparative Example 7

Formula 6-7 compound is used as the host in the EML.

(8) Comparative Example 8

Formula 1-2 compound is used as the host in the EML.

(9) Example 1

The compound H-1 is used as the host in the EML.

(10) Example 2

The compound H-2 is used as the host in the EML.

(11) Example 3

The compound H-4 is used as the host in the EML.

(12) Example 4

The compound H-5 is used as the host in the EML.

(13) Example 5

The compound H-6 is used as the host in the EML.

[Formula 5]

-continued
5-3
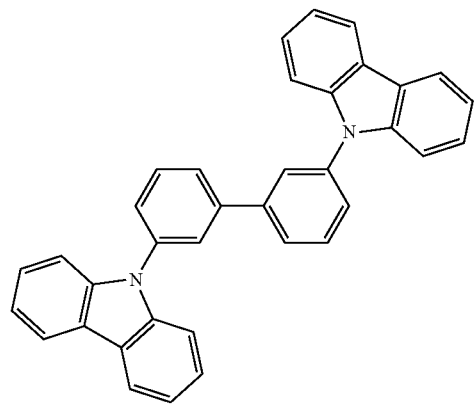
5-4
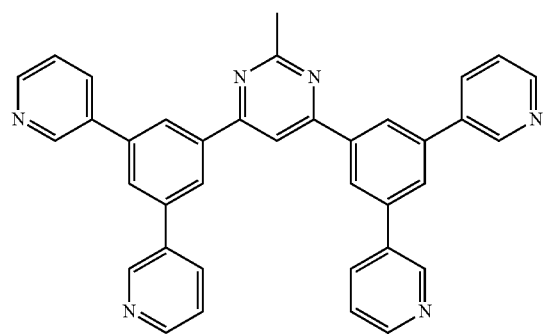
5-5
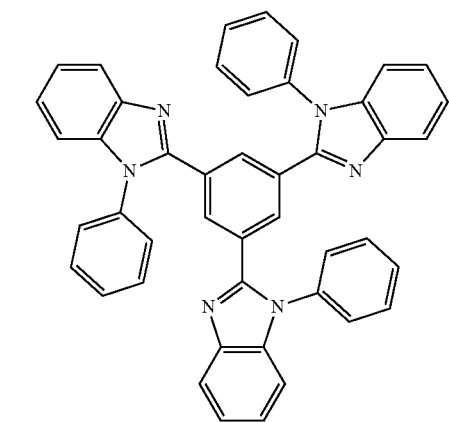
[Formula 6]
6-1
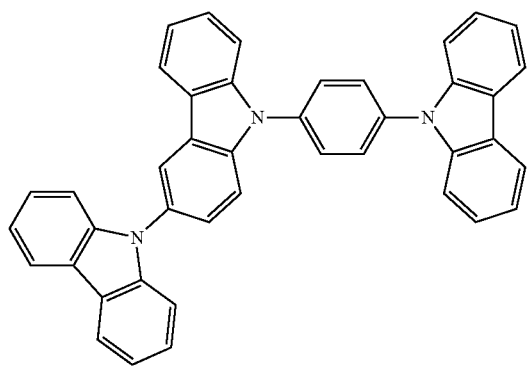
-continued
6-2
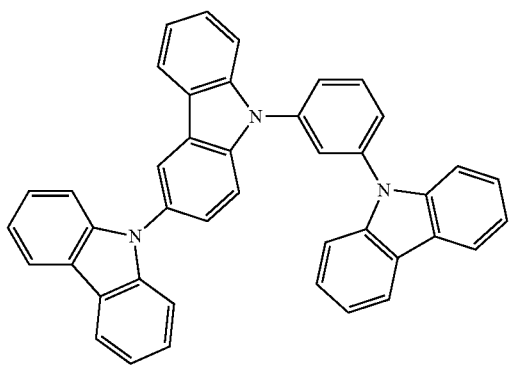
6-3
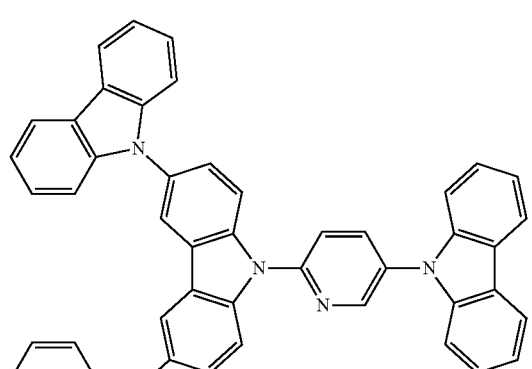
6-4
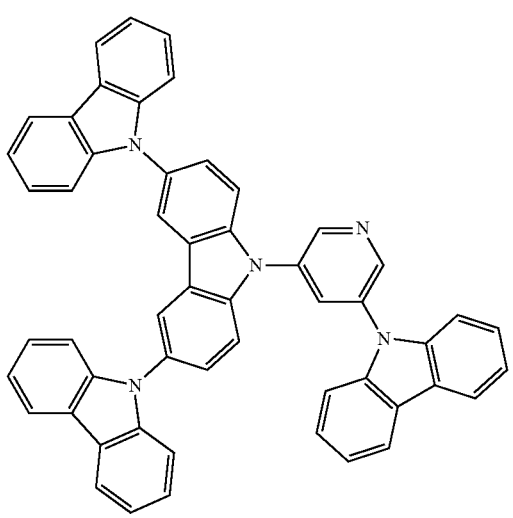

-continued

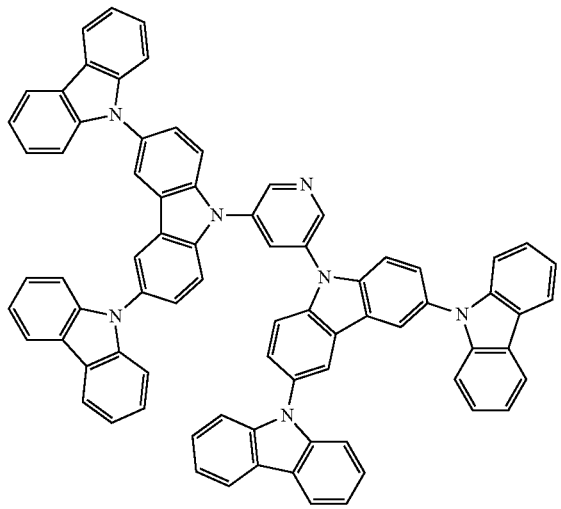

6-5

The properties of the organic light emitting diodes of Comparative Examples 1 to 8 and Examples 1 to 5 are measured and listed in Table 2. The voltage, the external quantum efficiency (EQE) and the color coordinate index are measured at 10 mA/cm$^2$, and the lifetime (L) is a relative value at 95% with respect to the initial brightness (300 nit).

TABLE 2

|       | V    | Cd/A | EQE (%) | EQE max | CIE x | CIE y | L   |
|-------|------|------|---------|---------|-------|-------|-----|
| Ref1  | 5.7  | 5.6  | 4.5     | 7.9     | 0.15  | 0.17  | 10  |
| Ref2  | 7.1  | 6.4  | 4.3     | 7.6     | 0.16  | 0.22  | 8   |
| Ref3  | 3.8  | 7.9  | 5.6     | 7.5     | 0.16  | 0.20  | 8   |
| Ref4  | 3.8  | 9.2  | 6.3     | 7.9     | 0.16  | 0.21  | 5   |
| Ref5  | 4.5  | 2.2  | 2.2     | 2.2     | 0.16  | 0.14  | 8   |
| Ref6  | 6.4  | 2.2  | 1.9     | 3.8     | 0.16  | 0.18  | 9   |
| Ref7  | 4.4  | 0.31 | 0.2     | 0.3     | 0.16  | 0.18  | 4   |
| Ref8  | 5.5  | 17.5 | 9.8     | 21.0    | 0.175 | 0.290 | <2  |
| Ex1   | 4.7  | 8.4  | 5.9     | 8.1     | 0.16  | 0.20  | 84  |
| Ex2   | 4.0  | 7.9  | 6.1     | 10.7    | 0.15  | 0.18  | 100 |
| Ex3   | 4.6  | 9.3  | 6.0     | 8.1     | 0.16  | 0.24  | 80  |
| Ex4   | 3.8  | 9.2  | 6.3     | 7.9     | 0.16  | 0.21  | 80  |
| Ex5   | 3.7  | 8.3  | 5.9     | 7.5     | 0.16  | 0.20  | 72  |

As shown in Table 2, the properties, e.g., the voltage and the efficiency, of the organic light emitting diodes of Ex1 to Ex5, which includes the organic compound of the present invention as the host, are improved. Particularly, in comparison to the organic light emitting diodes of Ref1 to Ref8, the lifetime of the organic light emitting diodes of Ex1 to Ex5 is remarkably improved.

Namely, since the organic compound of the present invention has high triplet energy, the emission efficiency of the organic light emitting diode and the OLED device is improved. In addition, since the organic compound of the present invention has high stability, the lifetime of the organic light emitting diode and the OLED device is increased.

It will be apparent to those skilled in the art that various modifications and variations can be made in the organic compound, the organic light emitting diode, and the OLED device using the same of the present disclosure without departing from the technical idea or scope of the disclosure. Thus, it is intended that the present disclosure cover the modifications and variations of this disclosure provided they come within the scope of the appended claims and their equivalents.

What is claimed is:

1. An organic compound of following formula:

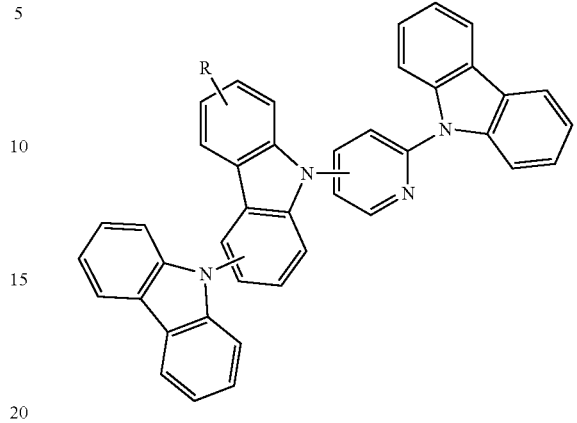

wherein R is carbazole.

2. The organic compound according to claim 1, wherein the organic compound is selected from the following:

H-4

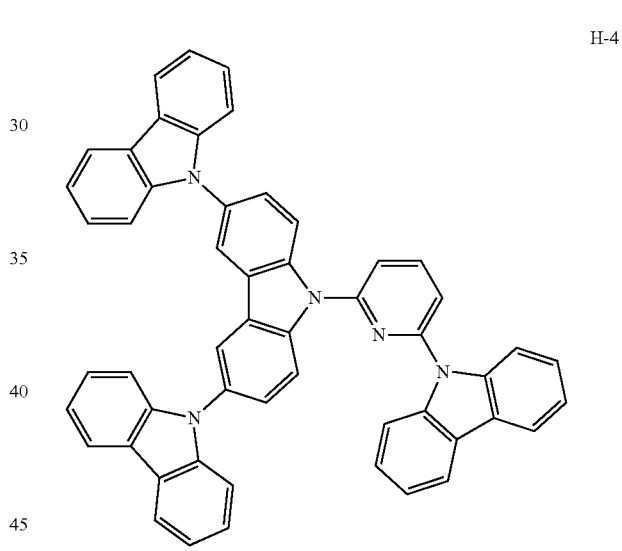

H-5

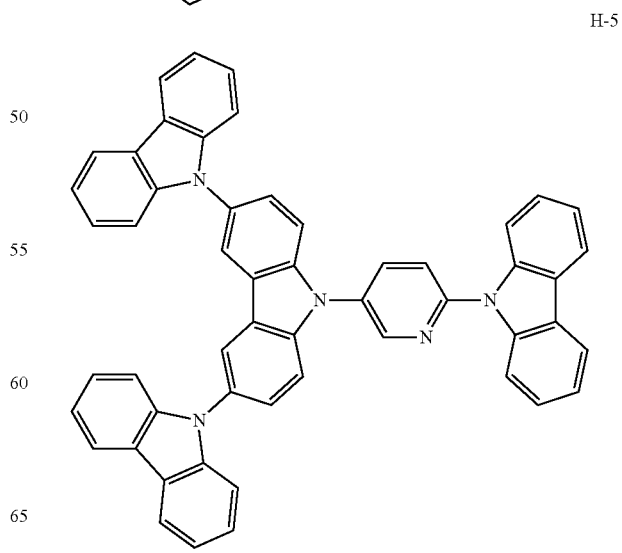

H-6

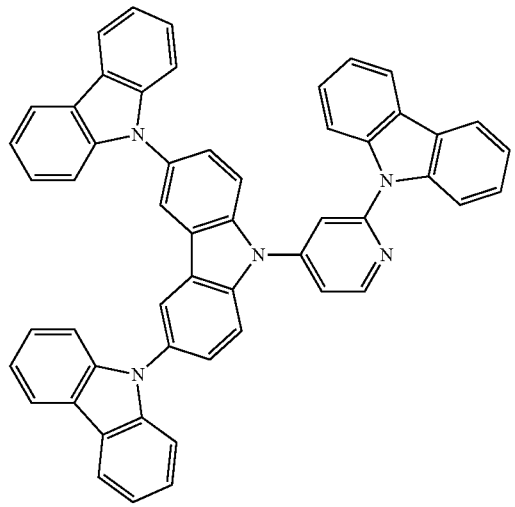

H-5

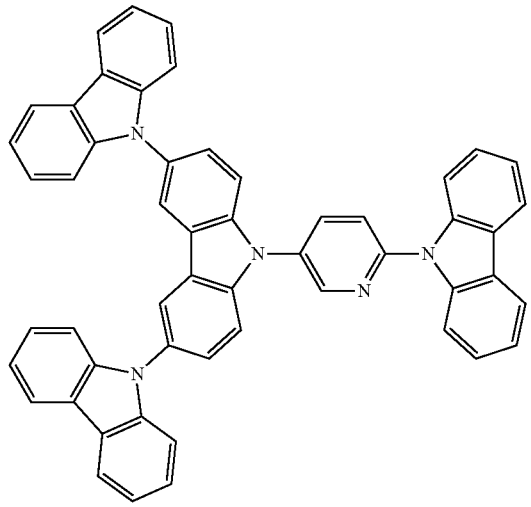

3. The organic compound according to claim 1, wherein the carbazole moiety substituted by R has a meta-position or a para-position with respect to a single carbazole moiety connected to a pyridine moiety.

4. An organic light emitting diode, comprising:
a first electrode;
a second electrode facing the first electrode; and
an organic emitting layer between the first and second electrodes and including the organic compound according to claim 1.

5. The organic light emitting diode according to claim 4, wherein the organic compound is selected from the following:

H-4

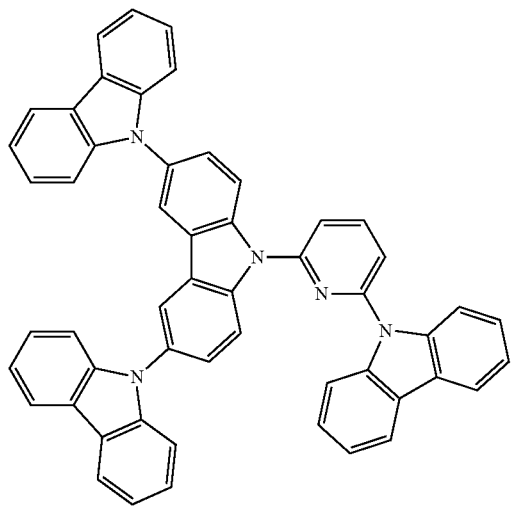

H-6

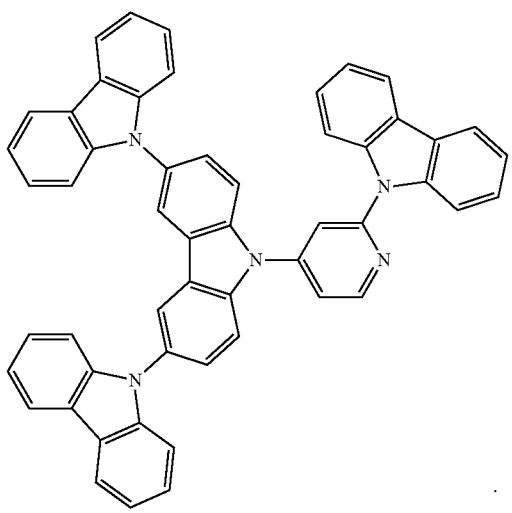

6. The organic light emitting diode according to claim 4, wherein the carbazole moiety substituted by R has a meta-position or a para-position with respect to a single carbazole moiety connected to a pyridine moiety.

7. An organic light emitting display device, comprising:

a substrate;

an organic light emitting diode over the substrate and including a first electrode, a second electrode facing the first electrode and an organic emitting layer between the first and second electrodes; and a thin film transistor between the substrate and the organic light emitting diode and connected to the organic light emitting diode, wherein the organic emitting layer includes the organic compound according to claim 1.

8. The organic light emitting display device according to claim 7, wherein the organic compound is selected from following:

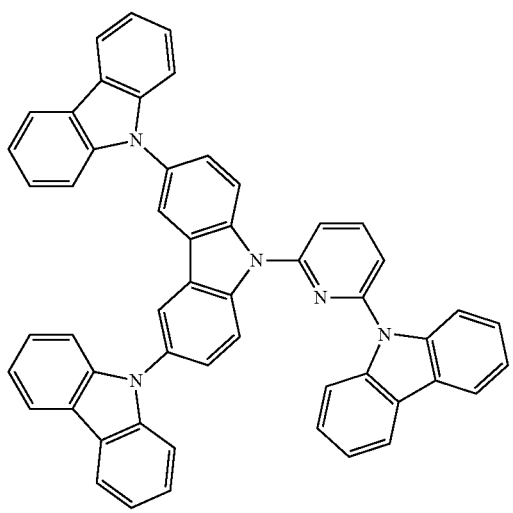

H-4

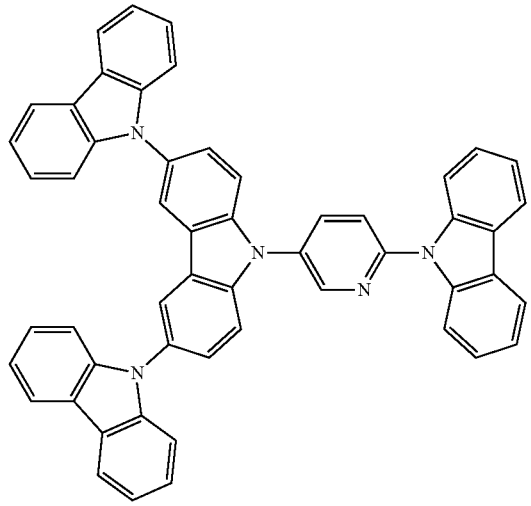

H-5

H-6

9. The organic light emitting display device according to claim 7, wherein the carbazole moiety substituted by R has a meta-position or a para-position with respect to a single carbazole moiety connected to a pyridine moiety.

10. The organic light emitting diode according to claim 4, wherein the organic emitting layer further includes a dopant selected from the following:

27
D-1
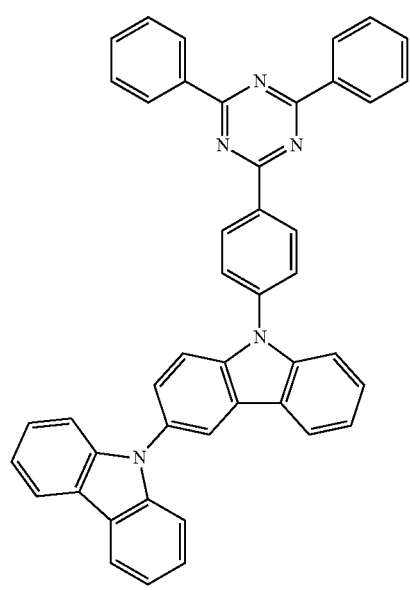
28
D-2
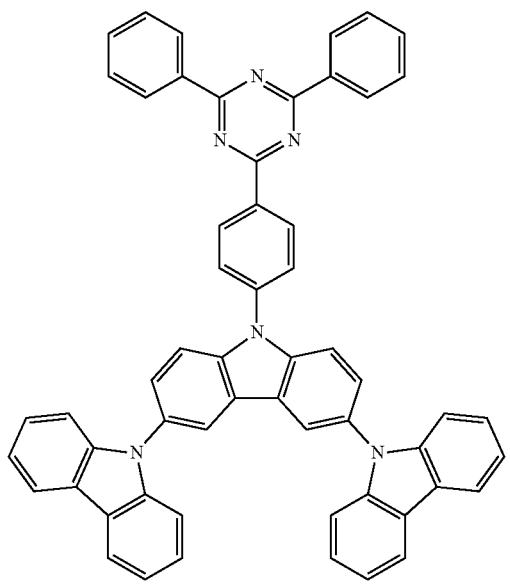
D-3
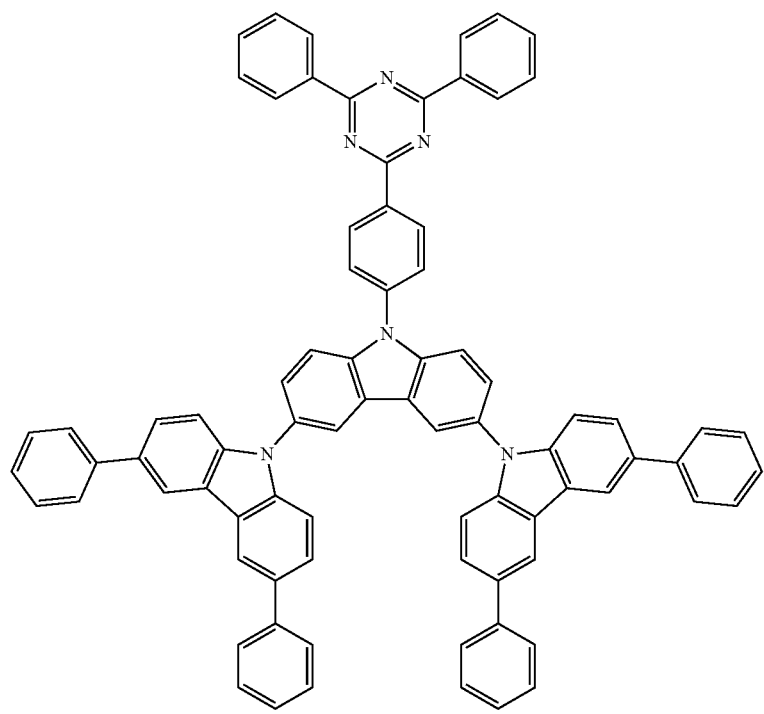

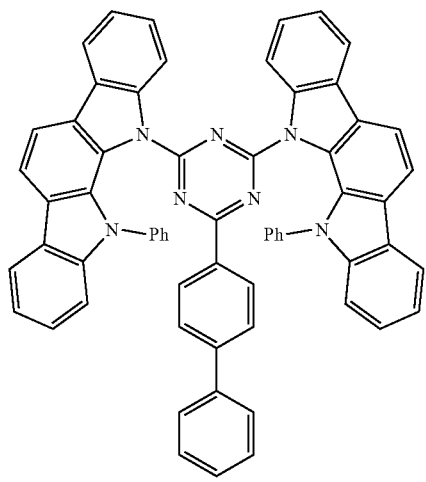
D-4
11. The organic light emitting display device according to claim 7, wherein the organic emitting layer further includes a dopant selected from the following:
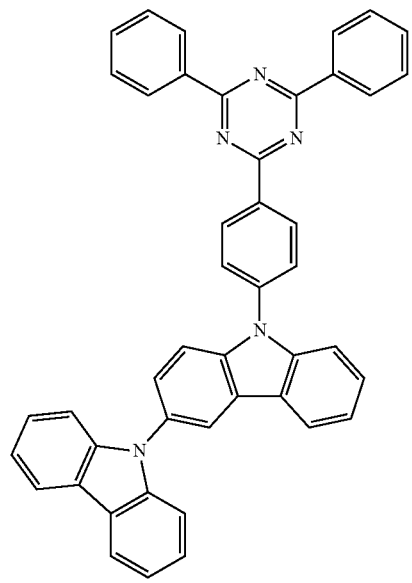
D-1
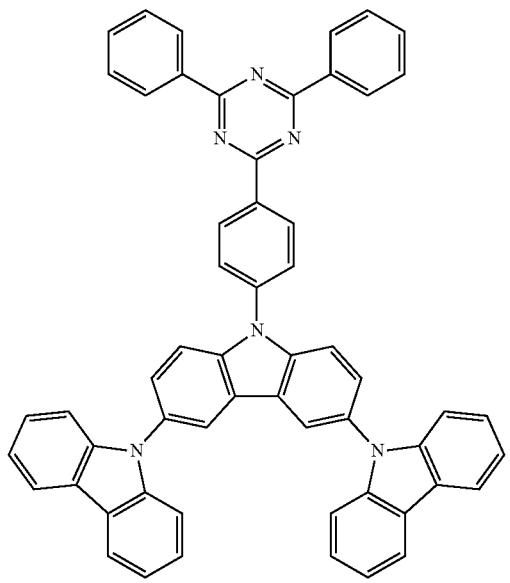
D-2

-continued
D-3
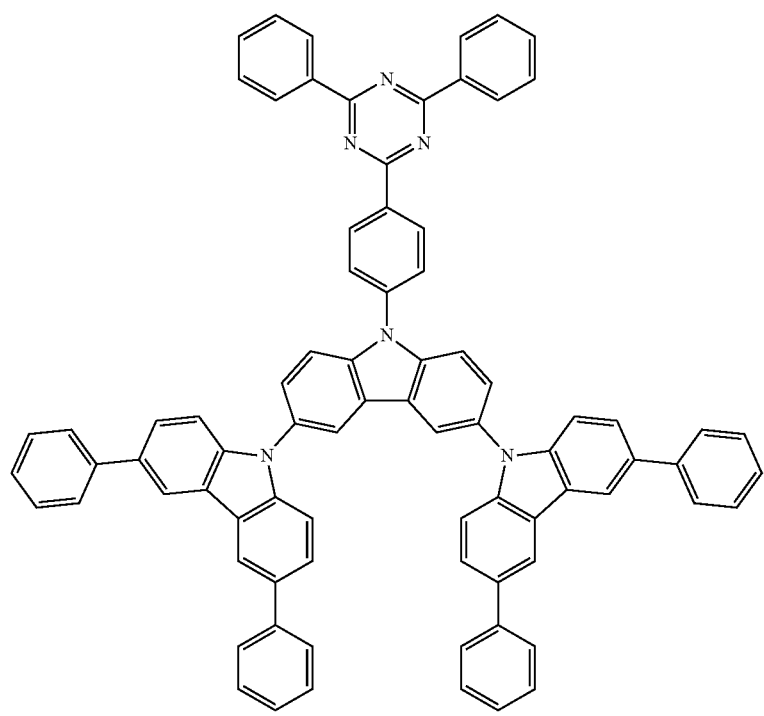
D-4
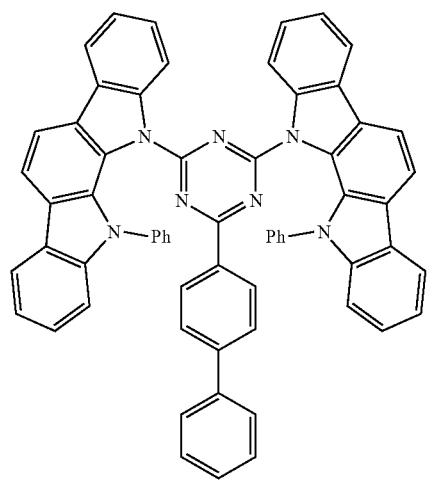
* * * * *